United States Patent
Smith

(10) Patent No.: US 7,422,327 B2
(45) Date of Patent: Sep. 9, 2008

(54) RETINAL TOPOGRAPHY DIFFRACTIVE FUNDUS LENS

(75) Inventor: Ronald T. Smith, Newport Coast, CA (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 11/618,837

(22) Filed: Dec. 31, 2006

(65) Prior Publication Data

US 2007/0171368 A1    Jul. 26, 2007

Related U.S. Application Data

(60) Provisional application No. 60/755,439, filed on Dec. 31, 2005.

(51) Int. Cl.
*A61B 3/14* (2006.01)
*A61B 3/10* (2006.01)

(52) U.S. Cl. .................................. 351/206; 351/205

(58) Field of Classification Search .......... 351/200–246
See application file for complete search history.

(56) References Cited

U.S. PATENT DOCUMENTS

| | | | | |
|---|---|---|---|---|
| 4,423,931 A | * | 1/1984 | Shapiro | 351/206 |
| 4,730,910 A | * | 3/1988 | Humphrey | 359/601 |
| 4,738,521 A | | 4/1988 | Volk | 351/205 |
| 4,900,144 A | | 2/1990 | Kobayashi | 351/206 |
| 7,048,379 B2 | * | 5/2006 | Miller et al. | 351/213 |
| 2006/0170867 A1 | * | 8/2006 | Koschmieder et al. | 351/213 |

* cited by examiner

*Primary Examiner*—Mohammed Hasan
(74) *Attorney, Agent, or Firm*—Armando Pastrana, Jr.

(57) ABSTRACT

Embodiments of the present invention provide a fundus lens. This fundus lens includes a first aspheric lens and a second aspheric lens and a diffractive optical element. This diffractive optical element is placed between the first and second aspheric lens and illuminated by an off access light source. The diffractive optical element contains a predetermined pattern which may be directed and imaged on a fundus. The first and second aspheric lenses are operable to gather light scattered by the fundus and provide the gathered light to a fundus camera. This fundus camera may then be operable to process the gathered light and determine the topography of the fundus.

8 Claims, 9 Drawing Sheets

RETINAL TOPOGRAPHY DIFFRACTIVE FUNDUS LENS

RELATED APPLICATIONS

This application claims the benefit of, priority to, and incorporates by reference in its entirety for all purposes U.S. Provisional Application No. 60/755,439 entitled "RETINAL TOPOGRAPHY DIFFRACTIVE FUNDUS LENS" filed on 31 Dec. 2005.

TECHNICAL FIELD OF THE INVENTION

The present invention relates generally to optical imaging systems and methods, and more particularly, a system and method for determining retinal topography.

BACKGROUND OF THE INVENTION

The shape of the normal eye is maintained by an internal fluid pressure of about 15 mm of mercury. That intraocular pressure (IOP) is controlled by the balance of flow of aqueous humor due to secretion from the ciliary body and drainage through the trabecular meshwork. In diseases of the eye, such as glaucoma, the balance is disturbed.

Typical retinal topography systems are bulky, complex and expensive systems. For example, U.S. Pat. No. 4,423,931 is entitled "Fundus Camera Accessory for Analysis of the Ocular Fundus Contour," discloses a method of illuminating the off-axis portion of the fundus with a pattern of linear stripes. Since the pattern is incident on the fundus at an angle relative to the fundus perpendicular, any bumps or depressions in the retinal surface will result in curved stripes. When these stripes are viewed through a fundus camera and analyzed, information can be derived about the topography of the retina. Unfortunately, this device requires a bulky off-axis illumination system that is attached to the fundus camera by means of a bracket. This adds to cost, weight, volume, and complexity of the system.

Changes in blood circulation and in the transport of cell components within the nerve fibers have been found in the optic disc during elevation of IOP. Optic nerve head tissue gradually dies, and a "caving in" or excavation of the optic disc deepens and gets wider as glaucoma damages the nerves. These changes in the topography of the optic disc surface are believed to precede visual field loss in many cases. In addition, the topographic changes can be measured objectively, whereas the other tests, such as visual field examination, are highly subjective. A change in optic disc topography is objective evidence that the prevailing IOP is too high for that eye.

Proposed use is for special value fundus lenses that can be use in conjunction with a standard ophthalmoscope or fundus camera for eye examinations or vitreoretinal surgeries.

SUMMARY OF THE INVENTION

The present invention provides a retinal topography system that substantially eliminates or reduces disadvantages and problems associated with previously developed systems and methods.

A first embodiment of the present invention provides a fundus lens. This fundus lens includes a first aspheric lens, a second aspheric lens, and a diffractive optical element (DOE). This diffractive optical element is placed between the first and second aspheric lens. When illuminated by an off access light source, the DOE allows a predetermined pattern to be imaged on the fundus (retina). The DOE stores the predetermined pattern to DOE imaged on a fundus. The first and second aspheric lenses are operable to gather light scattered by the fundus and provide the gathered light to a fundus camera. This fundus camera may then process the gathered light and determine the topography of the fundus.

Another embodiment provides a retinal topography imaging system that includes both a diffractive fundus lens and a fundus camera. The diffractive fundus lens is operable to both illuminate a fundus, such as a retina with a predetermined pattern, and be partially transparent so that a significant portion of the light scattered by the fundus will substantially transmit through the DOE without being disturbed. The fundus camera or other like imaging processing system, which is optically coupled to the diffractive fundus lens, is operable to analyze the gathered light scattered by the fundus to determine the topography of the fundus. The fundus lens essentially images light from the highly curved fundus or retina onto a flat plane in space. The two aspheric lenses provide this curved-to-flat object to image transformation. This flat planar intermediate image in space in then easily viewable by the fundus camera or other imaging system, since it is now a simple flat image. The DOE is designed to be as thin as possible and as transparent as possible to the light scattered off of the fundus which passes through the first aspheric lens, DOE, and second aspheric lens to the intermediate image. If the DOE causes some aberrations to the scattered beam passing through it, then the light will not focus down to a nice, sharp intermediate image. However, this problem can be solved by adjusting the design of aspheric lenses 1 and 2 so that the overall lens system—aspheric lens 1, the DOE, and aspheric lens 2—focus light to a sharp planar intermediate image.

Yet another embodiment provides a method to determine retinal topography. This method involves illuminating a DOE located within a diffractive fundus lens. The DOE contains a predetermined pattern which is able to be imaged on the retina with optical elements of the diffractive fundus lens. The retinal topography scatters light imaged in the predetermined pattern. At least a portion of this scattered light may be gathered with the diffractive fundus lens. This light is then processed to determine the retinal topography.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGUREs, like numerals being used to refer to like and corresponding parts of the various drawings.

To provide retinal topography information, a system and method that address the above identified needs is required. Embodiments of the present invention use a grid pattern or line pattern that is projected onto the fundus (retina) stored in the diffraction optical element (DOE). When illuminated with an appropriate light source (i.e., laser beam), the DOE projects a portion of the incident light onto the retina in the desired pattern. Viewing this line pattern with a fundus camera enables the observer to measure the topography of the retina.

Embodiments of the present invention provide a diffractive fundus lens that projects a grid pattern or line pattern onto the retina. This incorporates a diffraction optical element (DOE) and a laser diode that is either mounted in the fundus lens housing itself or is remotely located.

Figure 1:
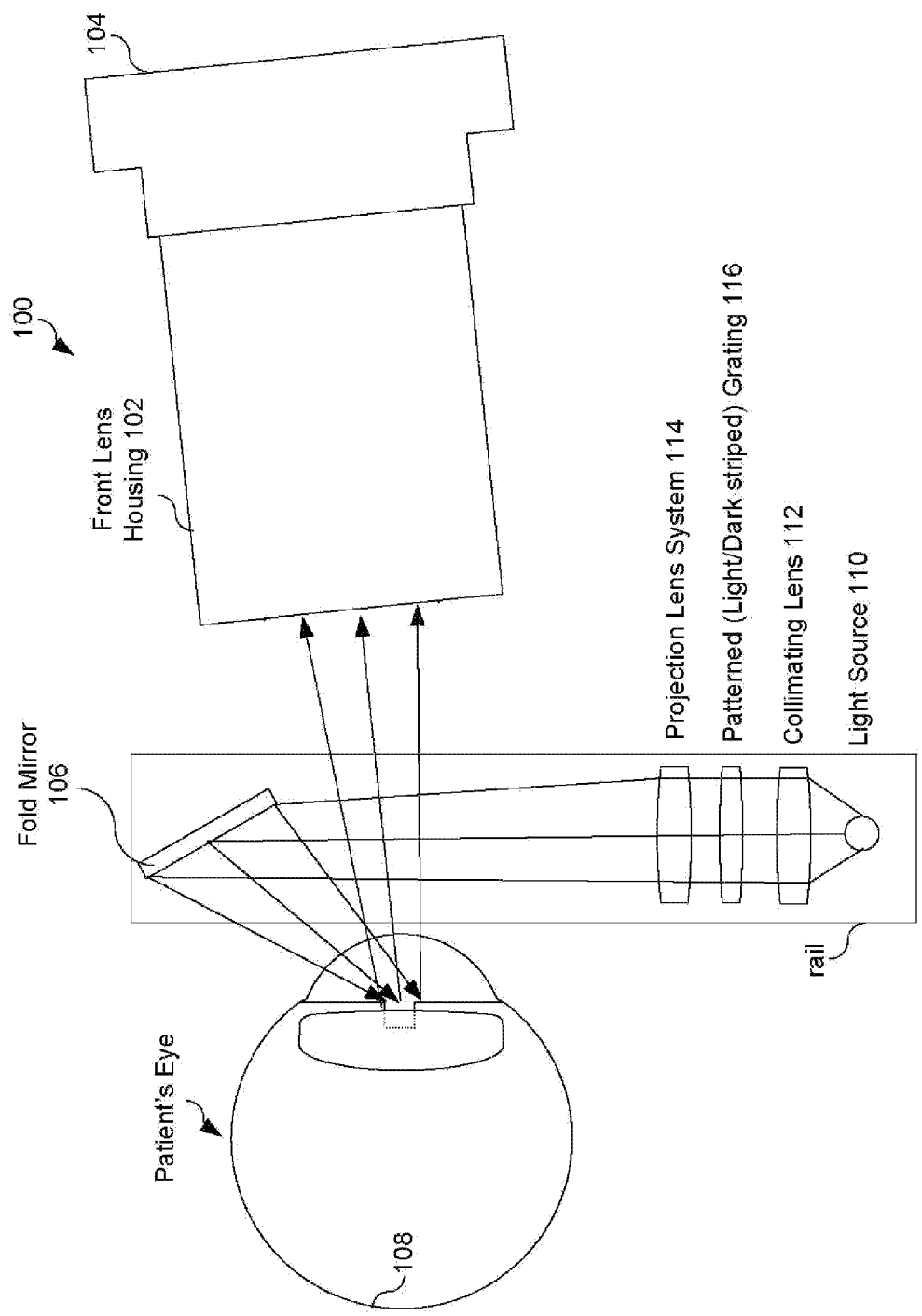
FIG. 1 provides a prior art retinal topography system.

FIG. 1 illustrates a double aspheric lens, such as those made by Volt Inc. and disclosed in U.S. Pat. No. 4,738,521 "Lens for Indirect Ophthalmoscopy." Here, optics in the imaging system are designed to look at the fundus directly requiring a more complex optical imaging system than is necessary if an intermediate fundus lens is used. Therefore, the fundus lens provided by embodiments of the present invention simplify the viewing of the fundus. Additionally, embodiments of the present invention provide the structure into which laser source, optics, and the DOE are mounted.

Figure 5:
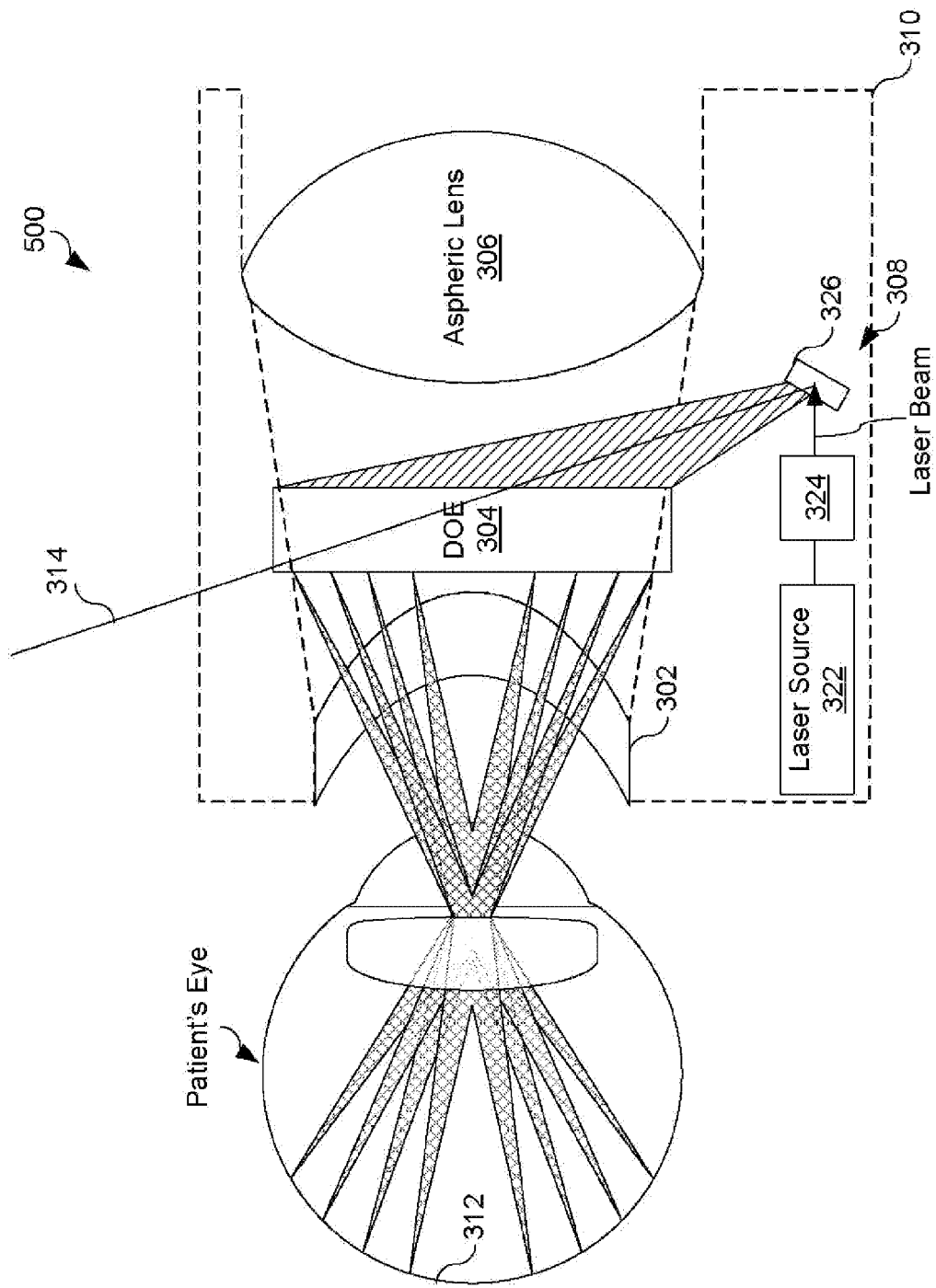
FIG. 5 provides a block diagram of a diffractive fundus lens in accordance with an embodiment of the present invention.

FIG. 5 depicts an embodiment that includes a laser diode, beam shaping optics, a fold mirror, and a DOE. The desired grid or line pattern information is recorded and stored in the DOE. When illuminated with light from the laser diode of FIG. 5, the DOE projects the laser light in the desired grid or line pattern on the retina. Only a portion of the illuminating light may be diffracted by the DOE since the DOE is not 100% efficient. Undiffracted light proceeds off-axis out of the on-axis optical beam path. In general, the light projected onto the retina as a grid or line pattern is incident on the retina at an off-axis angle relative to the retina normal. Therefore, any bumps or depressions in the retina) surface will create curves in the line pattern. The light incident on the retina will reflectively scatter off the retina, pass through the diffractive fundus lens (with only a small portion of light being diffracted off-axis by the DOE), and into a fundus camera or other like optical processing equipment where the curved line pattern can be analyzed to determine the topography of the retina.

The present invention utilizes a DOE within the fundus lens which is able to greatly reduce the size, cost and complexity when compared to traditional fundus retinal topography systems. By greatly reducing the cost, complexity and size, retinal topography becomes more available at a lower cost and is thus able to improve diagnoses of various conditions of the eye.

FIG. 1 provides the prior art solution that is able to measure the topography of a patient's retina. This provided method is a rather large and complex system that includes a fundus camera 104 and pattern imaging optics 106 to image a pattern on the fundus or retina 108 of the patient's eye. Image patterning optics 106 includes a light source 110, a first and second lens, 112 and 114, a patterned grating 116, and a fold mirror. Fundus lens 102 gathers light from the patient's eye which may be then processed or captured using camera 104.

Figure 2:
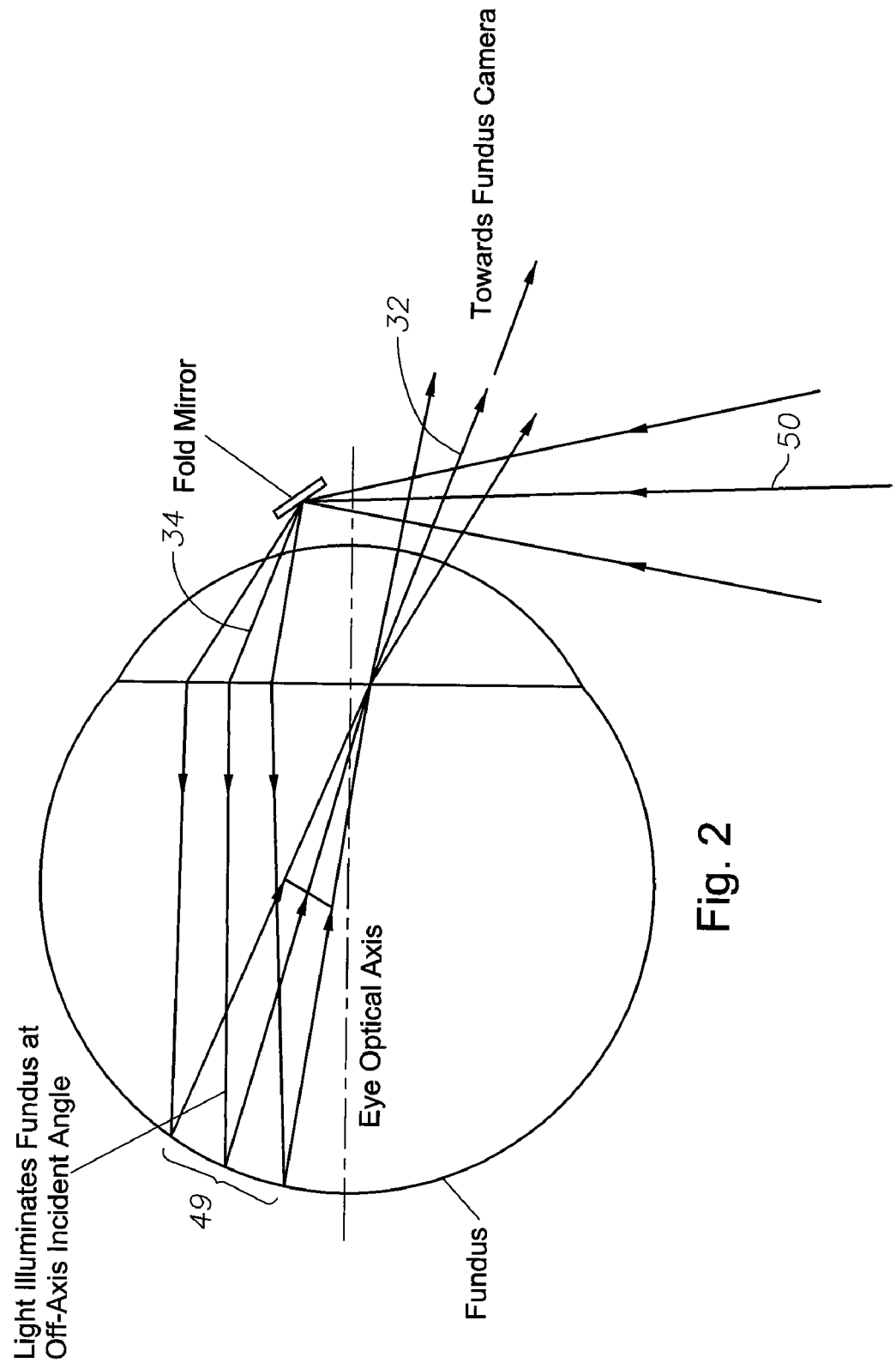
FIG. 2 depicts a prior art off-axis illumination of the fundus in order to determine retinal topography.

FIG. 2 illustrates that any stripe pattern incident on the fundus at an angle relative to the fundus perpendicular will result in curved stripes and any bumps or depressions in the retinal or fundus surface are illuminated by the pattern. The prior art system shown requires a bulky off-axis illumination system 106 that may be attached to the fundus camera by means of a bracket adding cost, weight and complexity to the system.

Figure 3:
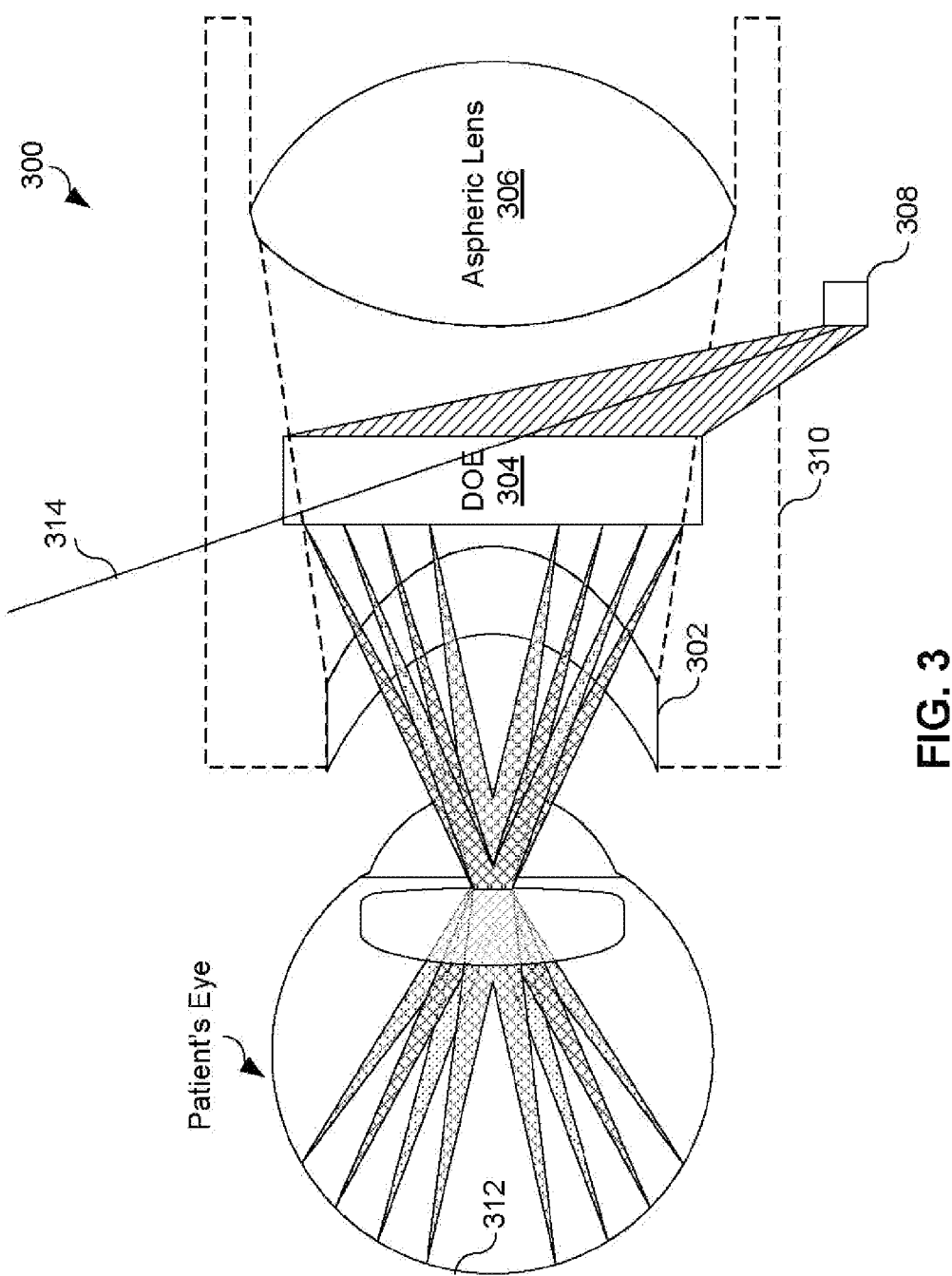
FIG. 3 depicts a diffracted fundus lens in accordance with an embodiment of the present invention.

FIG. 2 depicts the off-axis illumination of the fundus in order to determine retinal topography in accordance with an embodiment of the present invention. FIG. 3 describes a diffractive fundus lens 300 in accordance with an embodiment of the present invention. This diffractive fundus lens includes a first aspheric lens 302, a diffraction optical element (DOE) 304, a second aspheric lens 306, and an illuminating light source 308 wherein elements 302 through 308 may be contained within a lens body 310. DOE 304 is operable to store a predetermined pattern therein. This predetermined pattern may be a desired grid or line pattern which is recorded and stored within DOE 304. When the DOE is illuminated by light source 308, the DOE may project the stored pattern on the fundus or retina 312. Only a portion of the illuminating light produced by light source 308 is diffracted by DOE 302 as DOE 302 may not be 100% efficient. The undiffracted portion of the light from light source 308 proceeds off axis along the on axis optical beam path 314. This inefficiency allows light gathered by the diffractive fundus lens to be passed to the fundus camera with little loss being caused by the DOE.

In general, light projected onto retina 312 of a patient's eye in the predetermined pattern is incident on retina 312 at an off axis angle relative to the retina normal as shown in FIG. 2. Therefore, any bumps or depressions in the retina surface will create curved lines in the pattern imaged on the retina. This is described with reference to FIG. 4.

Figure 4:
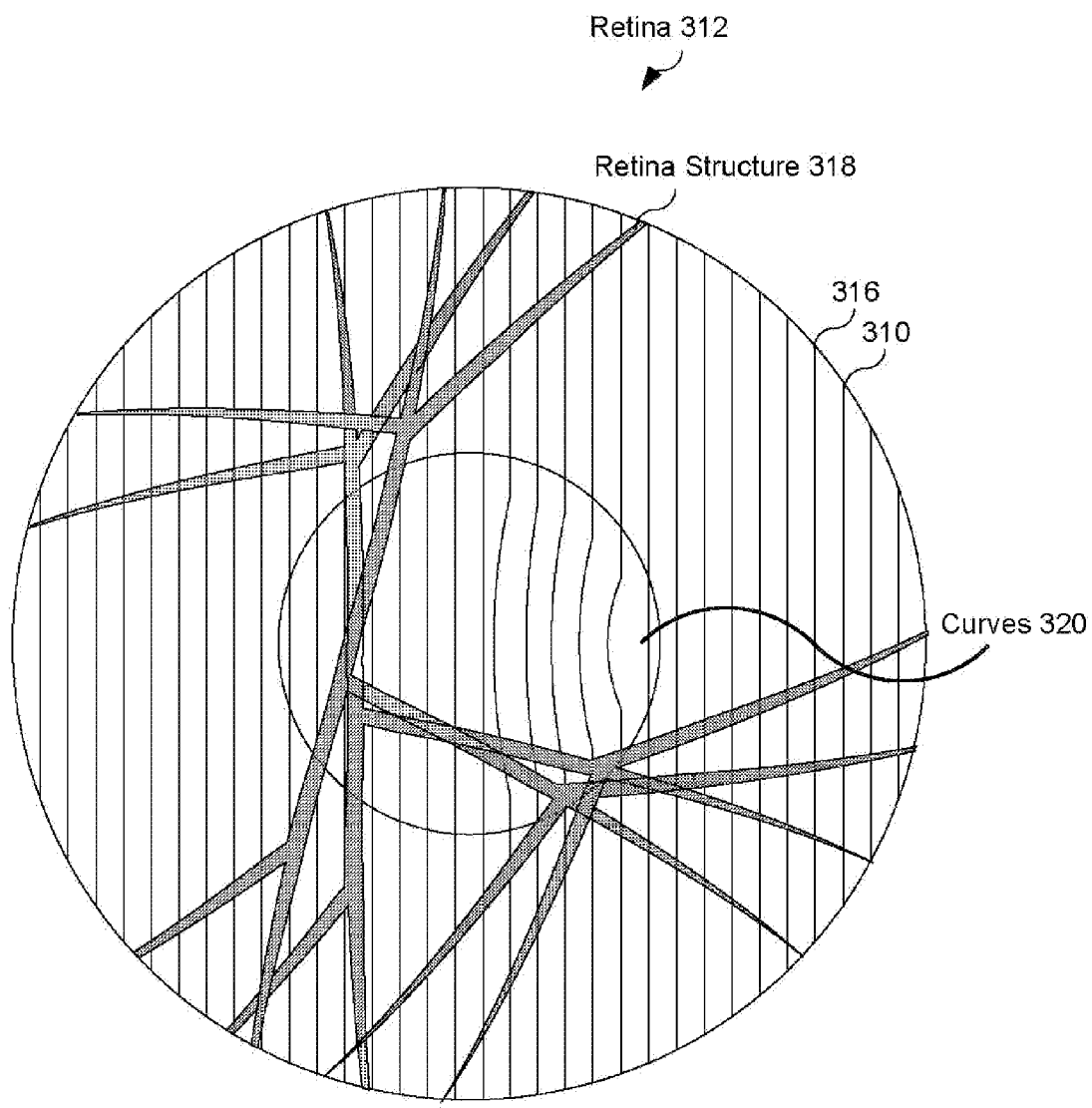
FIG. 4 depicts how bumps or depressions in the fundus or retinal surface may distort a pattern imaged on the retinal surface in accordance with an embodiment of the present invention.

FIG. 4 depicts a retina 312 illuminated with a stripe pattern which may be used to determine the retinal topography. Stripes 316 project a pattern as depicted in FIG. 4 on the retina. Also, the structure 318 of the retina may be imaged as well. Curves 320 within stripes 316 indicate non-fat retinal topography. The fundus camera, coupled to the diffractive lens, is operable to process the imaged pattern on the retina to determine the retinal topography. (Rob: 310 is not defined here. Is it different than 316? If not, it should be deleted from FIG. 4)

FIG. 5 provides more detail of diffractive fundus lens 500. Here, off axis light source 308 is depicted as a laser source 322, such as but not limited to a red laser diode and other optical elements which perform beam shaping and redirecting functions. For example, beam shaping optics 324 and folded mirror 326 may be used to direct and illuminate DOE 304 from off the optical axis of the diffractive element. Other like methods may be used to properly illuminate DOE 304. Elements 322, 324 and 326 should reside within lens body 310. Light from the DOE passes straight through aspheric lens without bending. In reality, however, the light bends. The light delivered to each stripe on the retina came from a large portion of the DOE surface which is not shown well in FIG. 5.

Figure 6:
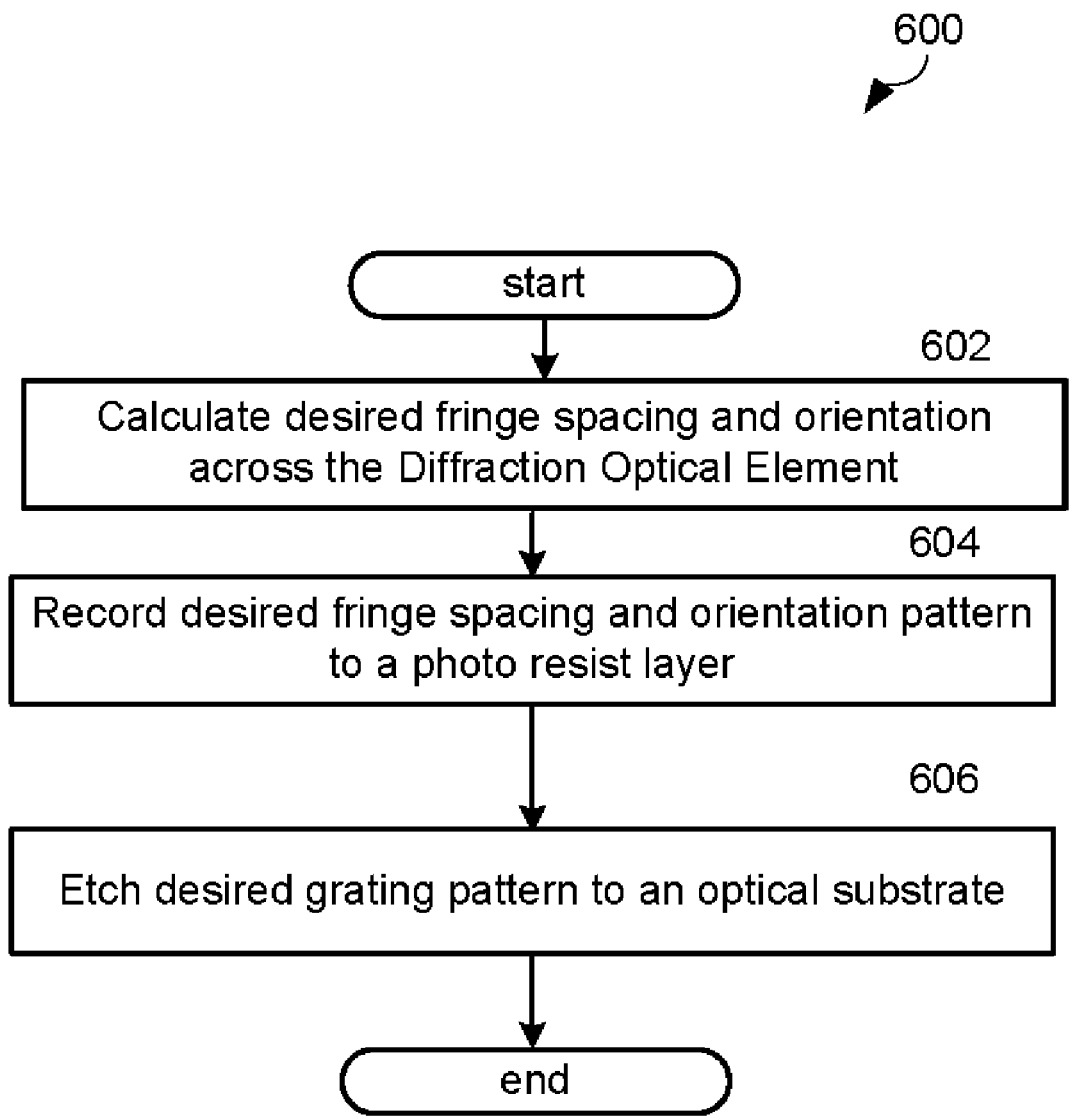
FIG. 6 provides a logic flow diagram illustrating a first means of producing a diffractive optical element in accordance with an embodiment of the present invention.

DOE 304 may contain either a computer generated optically recorded predetermined pattern or other like pattern. This pattern may be computer generated or optically recorded using a holographic exposure set up. The computer-generated approach may include steps as illustrated in FIG. 6. Operations 600 begin with the calculation of the desired fringe spacing and fringe orientation across the element that will cause the element to diffract a predetermined defined incident beam into a desired pattern on the retina in step 602. In step 604 the desired fringe spacing and fringe orientation pattern may be recorded within a photo-resist laser. Using photolithographic techniques, step 608 etches the desired grading pattern to a suitable optical substrate.

Figure 7:
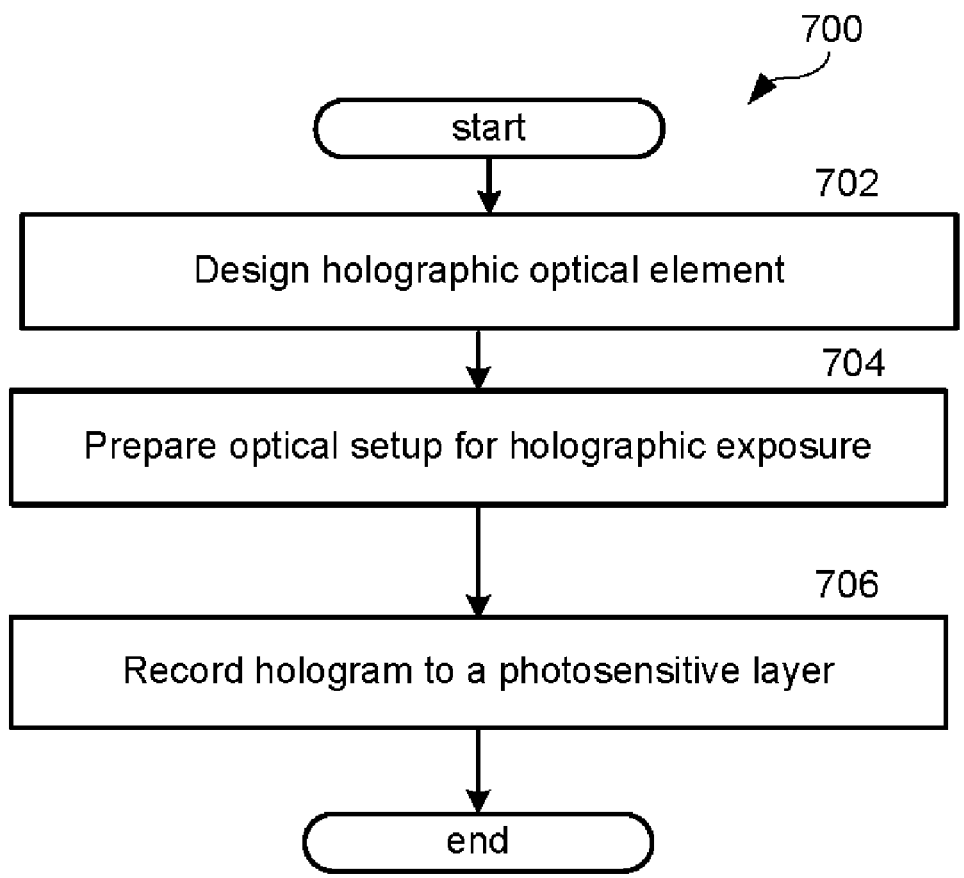
FIG. 7 provides a second logic flow diagram operable to produce a diffractive optical element in accordance with an embodiment of the present invention.

FIG. 7 depicts operations 700 which generally describe a holographic approach to recording the predetermined pattern within the defractive optical element. In step 702, a holographic optical element is designed such that it will diffract the defined incident beam from light source 308 into the desired pattern on retina 312. In step 704 necessary optics for the holographic exposure are arranged. In step 706, a photosensitive layer of holographic film is inserted into the exposure system and used to record the hologram.

Figure 8:
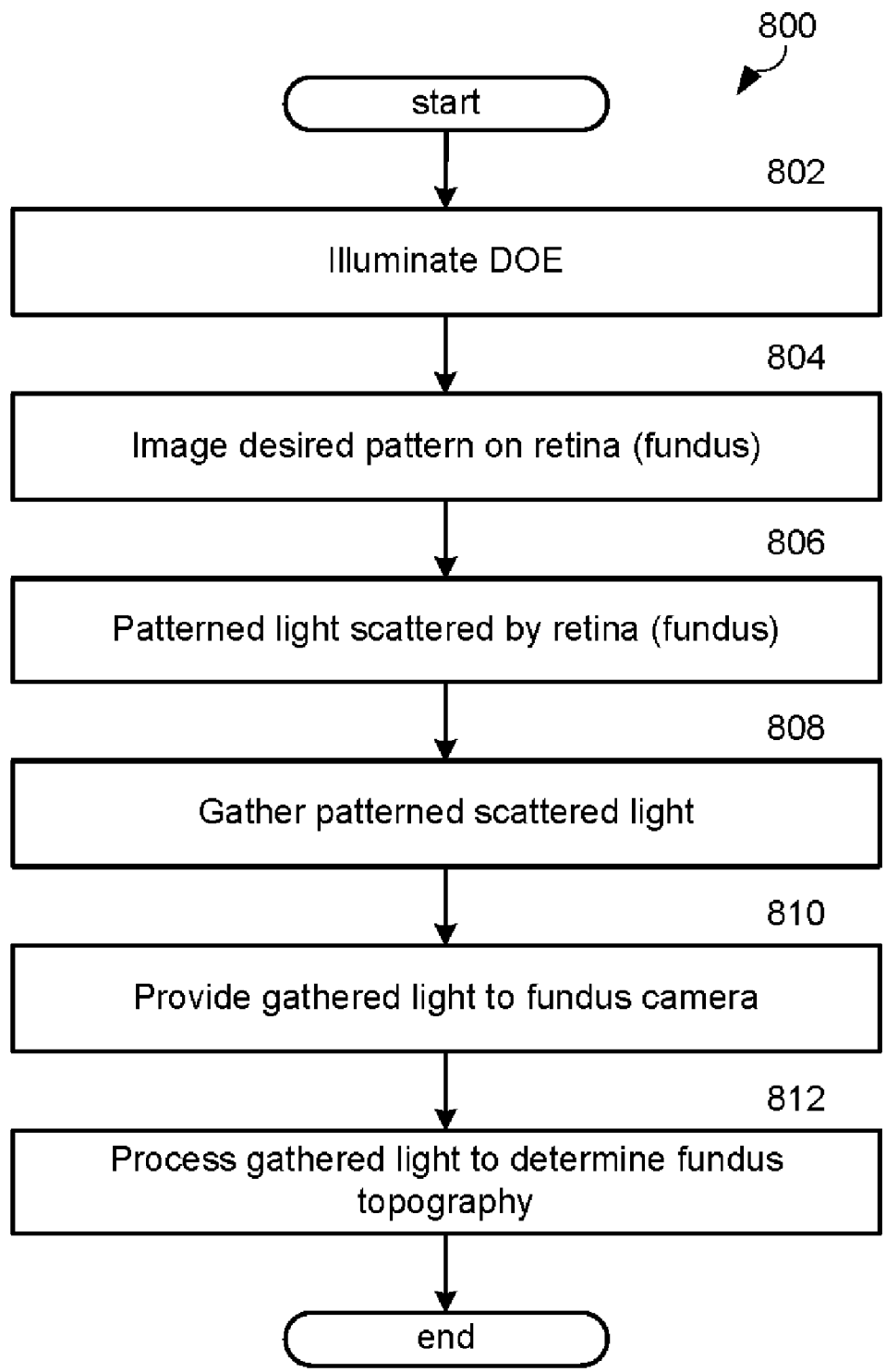
FIG. 8 provides a logic flow diagram of a method operable to determine retinal topography in accordance with an embodiment of the present invention.
Figure 9:
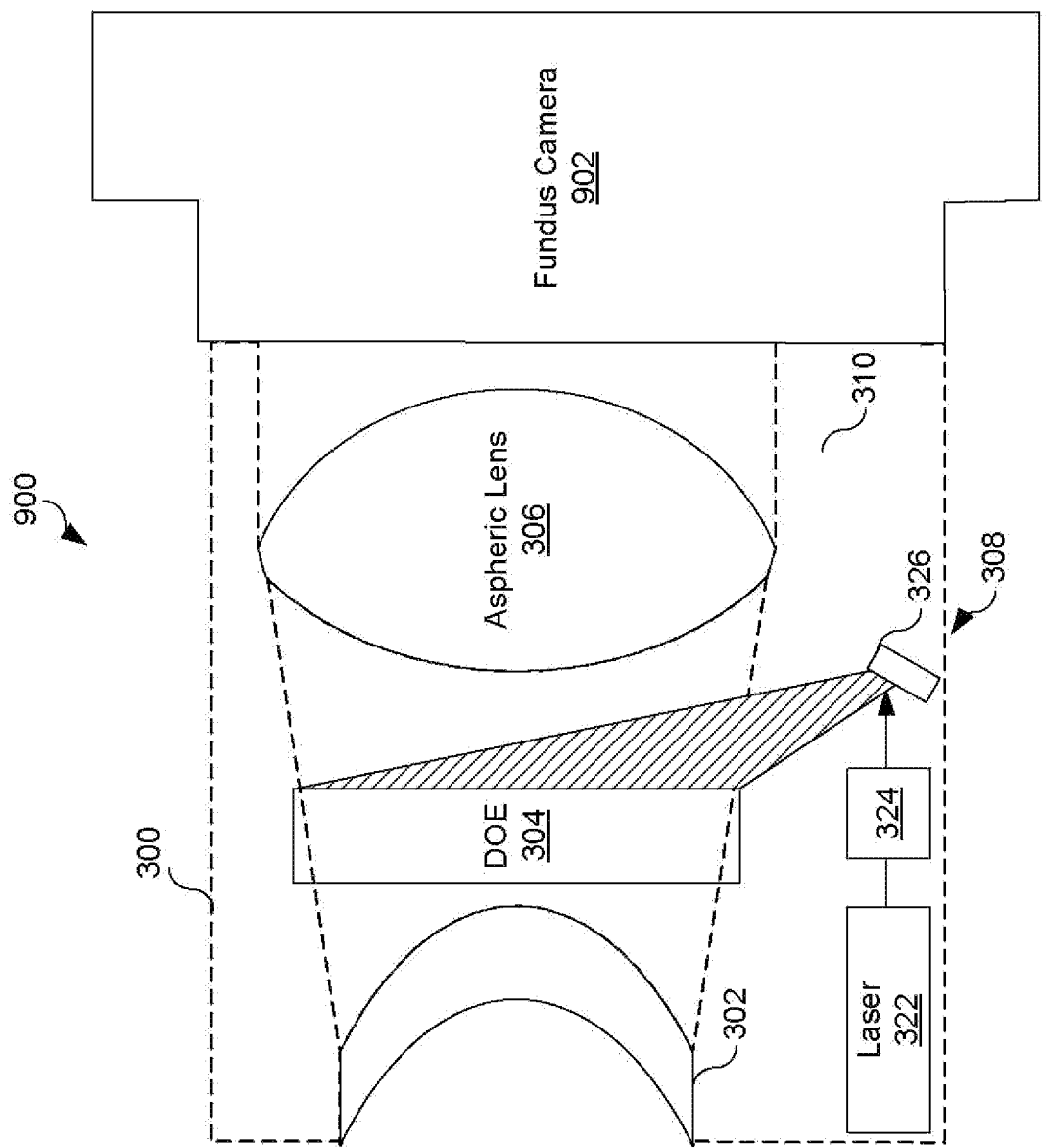
FIG. 9 provides a block diagram of a retinal topography imaging system in accordance with an embodiment of the present invention.

FIG. 8 provides a logic flow diagram illustrating one embodiment of the present invention operable to determine a retinal topography. This method involves illuminating a DOE containing a predetermined optical pattern in step 802. This DOE, which may contain a holographic pattern, is illuminated with an appropriate light source, such as a laser beam. When illuminated properly, the DOE projects a light onto the retina in a desired pattern in step 804. Step 804 may further include focusing the pattern on the retina with a fundus lens. In step 806, the retina scatters the projected pattern imaged. In step 808, at least a portion of the scattered light is gathered with the first aspheric lens and second aspheric lens. This light is then provided to a fundus camera in step 810, where the fundus camera in step 812 processes the gathered scattered light to determine the retinal topography. The inefficiency of the DOE allows the light gathered by the fundus lens to substantially pass the pattern scattered by the retina FIG. 9 depicts a retinal topography imaging system 900 that includes a diffractive fundus lens 300 such as that described with reference to FIG. 3 and FIG. 5 and a fundus camera 902. Fundus camera 902 optically couples to diffractive fundus lens 300. The fundus camera may be an optical or a digital system. This system may contain processing circuitry operable to analyze the imaged pattern and determine the retinal topography.

Although the present invention is described in detail, it should be understood that various changes, substitutions and alterations can be made hereto without departing from the spirit and scope of the invention as described by the appended claims.

What is claimed is:

1. A diffractive fundus lens, comprising:
   a first aspheric lens;
   a second aspheric lens;
   an off-axis light source;
   a diffractive optical element, wherein the DOE is illuminated by the off-axis light source; and
   wherein:
   the DOE, when illuminated, projects a desired pattern on a fundus;
   the first and second aspheric lenses are operable to gather light scattered by the fundus, and direct the gathered light into a fundus camera.

2. The diffractive fundus lens of claim 1, wherein the off-axis light source further comprises:
   a laser source operable to produce laser light; and
   at least one optical element operable to direct the laser light to the DOE.

3. The diffractive fundus lens of claim 1, wherein the desired pattern is stored within the DOE.

4. The diffractive fundus lens of claim 3, wherein the DOE stores the desired pattern holographically.

5. The diffractive fundus lens of claim 3, wherein the desired pattern is a computer generated pattern.

6. The diffractive fundus lens of claim 1, wherein the DOE has a low efficiency.

7. The diffractive fundus lens of claim 1, wherein the fundus camera analyzes the gathered light to determine the topography of the fundus.

8. The diffractive fundus lens of claim 1, wherein the fundus comprises an optical retina.

* * * * *